United States Patent
Allen, IV

(10) Patent No.: US 11,871,983 B2
(45) Date of Patent: *Jan. 16, 2024

(54) SURGICAL INSTRUMENT WITH SENSOR

(71) Applicant: Covidien LP, Mansfield, MA (US)

(72) Inventor: James D. Allen, IV, Broomfield, CO (US)

(73) Assignee: Covidien LP, Mansfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/403,971

(22) Filed: Aug. 17, 2021

(65) Prior Publication Data

US 2021/0369329 A1 Dec. 2, 2021

Related U.S. Application Data

(63) Continuation of application No. 16/899,678, filed on Jun. 12, 2020, now Pat. No. 11,090,112, which is a
(Continued)

(51) Int. Cl.
*A61B 18/14* (2006.01)
*A61B 34/00* (2016.01)
(Continued)

(52) U.S. Cl.
CPC .......... *A61B 18/1445* (2013.01); *A61B 34/30* (2016.02); *A61B 34/76* (2016.02);
(Continued)

(58) Field of Classification Search
None
See application file for complete search history.

(56) References Cited

U.S. PATENT DOCUMENTS

D249,549 S 9/1978 Pike
D263,020 S 2/1982 Rau, III
(Continued)

FOREIGN PATENT DOCUMENTS

CN 201299462 Y 9/2009
DE 2415263 A1 10/1975
(Continued)

OTHER PUBLICATIONS

Dulemba et al. "Use of a Bipolar Electrothermal Vessel Sealer in Laparoscopically Assisted Vaginal Hysterectomy" Sales/Product Literature; Jan. 2004. (1 page).
(Continued)

*Primary Examiner* — Ronald Hupczey, Jr.
(74) *Attorney, Agent, or Firm* — Carter, DeLuca & Farrell LLP

(57) ABSTRACT

A surgical instrument includes a housing, a shaft extending distally from the housing, an end effector disposed at a distal end of the shaft, an actuator operably coupled to the housing, an actuation assembly, and a sensor module. The actuation assembly extends through the housing and the shaft and includes a distal end operably coupled to the end effector or a component associated therewith, a proximal end operably coupled to the actuator, and a spring. Actuation of the actuator manipulates the end effector or deploys the component relative thereto. The sensor module is disposed within the housing and configured to sense a property of the spring indicative of an amount the spring has been compressed. The sensor module is further configured, based upon the sensed property, to determine a condition of the end effector or the relative position of the component.

17 Claims, 8 Drawing Sheets

Related U.S. Application Data continuation of application No. 15/401,227, filed on Jan. 9, 2017, now Pat. No. 10,695,123.

(60) Provisional application No. 62/288,962, filed on Jan. 29, 2016.

(51) Int. Cl.
| | | |
|---|---|---|
| *A61B 90/00* | (2016.01) | |
| *A61B 18/00* | (2006.01) | |
| *A61B 17/00* | (2006.01) | |
| *A61B 34/30* | (2016.01) | |

(52) U.S. Cl.
CPC ............ *A61B 2017/00115* (2013.01); *A61B 2018/00642* (2013.01); *A61B 2018/00684* (2013.01); *A61B 2018/00773* (2013.01); *A61B 2018/00875* (2013.01); *A61B 2018/1455* (2013.01); *A61B 2090/065* (2016.02)

(56) References Cited

U.S. PATENT DOCUMENTS

| | | |
|---|---|---|
| D295,893 S | 5/1988 | Sharkany et al. |
| D295,894 S | 5/1988 | Sharkany et al. |
| D298,353 S | 11/1988 | Manno |
| D299,413 S | 1/1989 | DeCarolis |
| D343,453 S | 1/1994 | Noda |
| D348,930 S | 7/1994 | Olson |
| D349,341 S | 8/1994 | Lichtman et al. |
| D354,564 S | 1/1995 | Medema |
| D358,887 S | 5/1995 | Feinberg |
| D384,413 S | 9/1997 | Zlock et al. |
| H1745 H | 8/1998 | Paraschac |
| 5,833,605 A | 11/1998 | Shah |
| D402,028 S | 12/1998 | Grimm et al. |
| D408,018 S | 4/1999 | McNaughton |
| D416,089 S | 11/1999 | Barton et al. |
| D424,694 S | 5/2000 | Tetzlaff et al. |
| D425,201 S | 5/2000 | Tetzlaff et al. |
| 6,056,735 A | 5/2000 | Okada et al. |
| H1904 H | 10/2000 | Yates et al. |
| D449,886 S | 10/2001 | Tetzlaff et al. |
| D453,923 S | 2/2002 | Olson |
| D454,951 S | 3/2002 | Bon |
| D457,958 S | 5/2002 | Dycus et al. |
| D457,959 S | 5/2002 | Tetzlaff et al. |
| H2037 H | 7/2002 | Yates et al. |
| D465,281 S | 11/2002 | Lang |
| D466,209 S | 11/2002 | Bon |
| D493,888 S | 8/2004 | Reschke |
| D496,997 S | 10/2004 | Dycus et al. |
| D499,181 S | 11/2004 | Dycus et al. |
| D502,994 S | 3/2005 | Blake, III |
| D509,297 S | 9/2005 | Wells |
| D525,361 S | 7/2006 | Hushka |
| D531,311 S | 10/2006 | Guerra et al. |
| D533,274 S | 12/2006 | Visconti et al. |
| D533,942 S | 12/2006 | Kerr et al. |
| D535,027 S | 1/2007 | James et al. |
| D538,932 S | 3/2007 | Malik |
| D541,418 S | 4/2007 | Schechter et al. |
| D541,611 S | 5/2007 | Aglassinge |
| D541,938 S | 5/2007 | Kerr et al. |
| D545,432 S | 6/2007 | Watanabe |
| 7,232,440 B2 | 6/2007 | Dumbauld et al. |
| D547,154 S | 7/2007 | Lee |
| D564,662 S | 3/2008 | Moses et al. |
| D567,943 S | 4/2008 | Moses et al. |
| D575,395 S | 8/2008 | Hushka |
| D575,401 S | 8/2008 | Hixson et al. |
| D582,038 S | 12/2008 | Swoyer et al. |
| D617,900 S | 6/2010 | Kingsley et al. |
| D617,901 S | 6/2010 | Unger et al. |
| D617,902 S | 6/2010 | Twomey et al. |
| D617,903 S | 6/2010 | Unger et al. |
| D618,798 S | 6/2010 | Olson et al. |
| D621,503 S | 8/2010 | Otten et al. |
| D627,462 S | 11/2010 | Kingsley |
| D628,289 S | 11/2010 | Romero |
| D628,290 S | 11/2010 | Romero |
| 7,852,066 B2 | 12/2010 | Krammer |
| D630,324 S | 1/2011 | Reschke |
| D649,249 S | 11/2011 | Guerra |
| D649,643 S | 11/2011 | Allen, IV et al. |
| D661,394 S | 6/2012 | Romero et al. |
| D670,808 S | 11/2012 | Moua et al. |
| 8,359,082 B2 * | 1/2013 | Selkee ............... A61B 18/1492 606/41 |
| D680,220 S | 4/2013 | Rachlin |
| 9,084,608 B2 | 7/2015 | Larson et al. |
| 9,211,657 B2 | 12/2015 | Ackley et al. |
| 10,695,123 B2 * | 6/2020 | Allen, IV .......... A61B 18/1445 |
| 11,090,112 B2 * | 8/2021 | Allen, IV .......... A61B 18/1445 |
| 2004/0015163 A1 | 1/2004 | Buysse et al. |
| 2007/0173814 A1 | 7/2007 | Hixson et al. |
| 2009/0261804 A1 | 10/2009 | McKenna et al. |
| 2014/0074092 A1 | 3/2014 | Horner et al. |
| 2014/0221995 A1 | 8/2014 | Guerra et al. |
| 2014/0221999 A1 | 8/2014 | Cunningham et al. |
| 2014/0228842 A1 | 8/2014 | Dycus et al. |
| 2014/0230243 A1 | 8/2014 | Roy et al. |
| 2014/0236149 A1 | 8/2014 | Kharin et al. |
| 2014/0243811 A1 | 8/2014 | Reschke et al. |
| 2014/0243824 A1 | 8/2014 | Gilbert |
| 2014/0249528 A1 | 9/2014 | Hixson et al. |
| 2014/0250686 A1 | 9/2014 | Hempstead et al. |
| 2014/0257274 A1 | 9/2014 | McCullough, Jr. et al. |
| 2014/0257283 A1 | 9/2014 | Johnson et al. |
| 2014/0257284 A1 | 9/2014 | Artale |
| 2014/0257285 A1 | 9/2014 | Moua |
| 2014/0276803 A1 | 9/2014 | Hart |
| 2014/0284313 A1 | 9/2014 | Allen, IV et al. |
| 2014/0288549 A1 | 9/2014 | McKenna et al. |
| 2014/0288553 A1 | 9/2014 | Johnson et al. |
| 2014/0330308 A1 | 11/2014 | Hart et al. |
| 2014/0336635 A1 | 11/2014 | Hart et al. |
| 2014/0353188 A1 | 12/2014 | Reschke et al. |
| 2015/0018816 A1 | 1/2015 | Latimer |
| 2015/0025528 A1 | 1/2015 | Arts |
| 2015/0032106 A1 | 1/2015 | Rachlin |
| 2015/0051598 A1 | 2/2015 | Orszulak et al. |
| 2015/0051640 A1 | 2/2015 | Twomey et al. |
| 2015/0066026 A1 | 3/2015 | Hart et al. |
| 2015/0080880 A1 | 3/2015 | Sartor et al. |
| 2015/0080889 A1 | 3/2015 | Cunningham et al. |
| 2015/0082928 A1 | 3/2015 | Kappus et al. |
| 2015/0088122 A1 | 3/2015 | Jensen |
| 2015/0088126 A1 | 3/2015 | Duffin et al. |
| 2015/0088128 A1 | 3/2015 | Couture |
| 2015/0094714 A1 | 4/2015 | Lee et al. |
| 2017/0172608 A1 * | 6/2017 | Madan ........... A61B 17/320068 |

FOREIGN PATENT DOCUMENTS

| | | |
|---|---|---|
| DE | 02514501 A1 | 10/1976 |
| DE | 2627679 A1 | 1/1977 |
| DE | 03423356 C2 | 6/1986 |
| DE | 03612646 A1 | 4/1987 |
| DE | 3627221 A1 | 2/1988 |
| DE | 8712328 U1 | 2/1988 |
| DE | 8712328 U1 | 3/1988 |
| DE | 04303882 C2 | 2/1995 |
| DE | 04403252 A1 | 8/1995 |
| DE | 19515914 C1 | 7/1996 |
| DE | 19506363 A1 | 8/1996 |
| DE | 29616210 U1 | 11/1996 |
| DE | 19608716 C1 | 4/1997 |
| DE | 19751106 A1 | 5/1998 |
| DE | 19738457 A1 | 3/1999 |
| DE | 19751108 A1 | 5/1999 |
| DE | 19946527 C1 | 7/2001 |
| DE | 20121161 U1 | 4/2002 |
| DE | 10045375 C2 | 10/2002 |

(56) References Cited

FOREIGN PATENT DOCUMENTS

| | | |
|---|---|---|
| DE | 202007009165 U1 | 8/2007 |
| DE | 202007009317 U1 | 8/2007 |
| DE | 202007009318 U1 | 8/2007 |
| DE | 10031773 B4 | 11/2007 |
| DE | 202007016233 U1 | 1/2008 |
| DE | 19738457 B4 | 1/2009 |
| DE | 102004026179 B4 | 1/2009 |
| DE | 102008018406 B3 | 7/2009 |
| EP | 1281878 A1 | 2/2003 |
| EP | 1159926 A2 | 3/2003 |
| JP | 61501068 | 9/1984 |
| JP | 61501068 A | 5/1986 |
| JP | 1024051 A | 1/1989 |
| JP | 1147150 A | 6/1989 |
| JP | 6502328 | 3/1992 |
| JP | 65106 | 1/1993 |
| JP | 0540112 | 2/1993 |
| JP | H0540112 A | 2/1993 |
| JP | 0006030945 | 2/1994 |
| JP | 6121797 A | 5/1994 |
| JP | 6285078 A | 10/1994 |
| JP | 06343644 | 12/1994 |
| JP | 6511401 | 12/1994 |
| JP | H06343644 A | 12/1994 |
| JP | 07265328 | 10/1995 |
| JP | H07265328 A | 10/1995 |
| JP | 856955 | 3/1996 |
| JP | 08056955 | 3/1996 |
| JP | 080566955 A | 5/1996 |
| JP | 08252263 A | 10/1996 |
| JP | 8289895 A | 11/1996 |
| JP | 8317934 A | 12/1996 |
| JP | 8317936 A | 12/1996 |
| JP | 910223 A | 1/1997 |
| JP | 09000538 A | 1/1997 |
| JP | H0910223 A | 1/1997 |
| JP | 9122138 A | 5/1997 |
| JP | 0010000195 A | 1/1998 |
| JP | 10155798 A | 6/1998 |
| JP | 1147149 | 2/1999 |
| JP | 11070124 A | 3/1999 |
| JP | 11169381 A | 6/1999 |
| JP | 11192238 A | 7/1999 |
| JP | 11244298 | 9/1999 |
| JP | H11244298 A | 9/1999 |
| JP | 2000102545 A | 4/2000 |
| JP | 2000135222 A | 5/2000 |
| JP | 2000342599 A | 12/2000 |
| JP | 2000350732 A | 12/2000 |
| JP | 2001003400 A | 1/2001 |
| JP | 2001008944 | 1/2001 |
| JP | 2001029355 | 2/2001 |
| JP | 2001029356 | 2/2001 |
| JP | 2001003400 | 4/2001 |
| JP | 2001128990 A | 5/2001 |
| JP | 2001190564 A | 7/2001 |
| JP | 2002136525 A | 5/2002 |
| JP | 2002528166 A | 9/2002 |
| JP | 2003116871 A | 4/2003 |
| JP | 2003175052 A | 6/2003 |
| JP | 2003245285 A | 9/2003 |
| JP | 2004517668 A | 6/2004 |
| JP | 2004528869 A | 9/2004 |
| JP | 2005152663 A | 6/2005 |
| JP | 2005253789 A | 9/2005 |
| JP | 2005312807 A | 11/2005 |
| JP | 2006015078 A | 1/2006 |
| JP | 2006501939 A | 1/2006 |
| JP | 2006095316 A | 4/2006 |
| JP | 2008054926 A | 3/2008 |
| JP | 2011125195 A | 6/2011 |
| JP | H0630945 B2 | 11/2016 |
| JP | 6502328 B2 | 4/2019 |
| SU | 401367 A1 | 10/1973 |
| SU | 401367 A1 | 11/1974 |
| WO | 0036986 A1 | 6/2000 |
| WO | 0059392 A1 | 10/2000 |
| WO | 0115614 A1 | 3/2001 |
| WO | 0154604 A1 | 8/2001 |
| WO | 0245589 | 6/2002 |
| WO | 0245589 A2 | 6/2002 |
| WO | 2006021269 A1 | 3/2006 |
| WO | 2005110264 A2 | 4/2006 |
| WO | 2008040483 A1 | 4/2008 |
| WO | 2008090338 A1 | 7/2008 |
| WO | 2011018154 A1 | 2/2011 |

OTHER PUBLICATIONS

Rothenberg et al. "Use of the LigaSure Vessel Sealing System in Minimally Invasive Surgery in Children" Int'l Pediatric Endosurgery Group (IPEG) 2000. (1 page).

Craig Johnson, "Use of the LigaSure Vessel Sealing System in Bloodless Hemorrhoidectomy" Innovations That Work, Mar. 2000. (4 pages).

E. David Crawford "Use of a Novel Vessel Sealing Technology in Management of the Dorsal Veinous Complex" Sales/Product Literature 2000. (1 page).

McLellan et al. "Vessel Sealing for Hemostasis During Pelvic Surgery" Int'l Federation of Gynecology and Obstetrics FIGO World Congress 2000, Washington, D.C.. (1 page).

McLellan et al. "Vessel Sealing for Hemostasis During Gynecologic Surgery" Sales/Product Literature 1999. (1 page).

Heniford et al. "Initial Research and Clinical Results with an Electrothermal Bipolar Vessel Sealer" Oct. 1999. (1 page).

Michael Choti, "Abdominoperineal Resection with the LigaSure Vessel Sealing System and LigaSure Atlas 20 cm Open Instrument"; Innovations That Work, Jun. 2003.

Tinkcler L.F., "Combined Diathermy and Suction Forceps", Feb. 6, 1967 (Feb. 6, 1967), British Medical Journal Feb. 6, 1976, vol. 1, nr. 5431 p. 361, ISSN: 0007-1447.

Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center,Charlotte,NC; Date: Aug. 2003.

Peterson et al. "Comparison of Healing Process Following Ligation with Sutures and Bipolar Vessel Sealing" Surgical Technology International (2001).

"Electrosurgery: A Historical Overview" Innovations in Electrosurgery; Sales/Product Literature; Dec. 31, 2000. (6 pages).

Johnson et al. "Evaluation of a Bipolar Electrothermal Vessel Sealing Device in Hemorrhoidectomy" Sales/Product Literature; Jan. 2004. (1 page).

E. David Crawford "Evaluation of a New Vessel Sealing Device in Urologic Cancer Surgery" Sales/Product Literature 2000.

Johnson et al. "Evaluation of the LigaSure Vessel Sealing System in Hemorrhoidectormy" American College of Surgeons (ACS) Clinicla Congress Poster (2000).

Muller et al., "Extended Left Hemicolectomy Using the LigaSure Vessel Sealing System" Innovations That Work, Sep. 1999.

Kennedy et al. "High-burst-strength, feedback-controlled bipolar vessel sealing" Surgical Endoscopy (1998) 12:876-878.

Burdette et al. "In Vivo Probe Measurement Technique For Determining Dielectric Properties At VHF Through Microwave Frequencies", IEEE Transactions on Microwave Theory and Techniques, vol. MTT-28, No. 4, Apr. 1980 pp. 414-427.

Carus et al., "Initial Experience With the LigaSure Vessel Sealing System in Abdominal Surgery" Innovations That Work, Jun. 2002.

W. Scott Helton, "LigaSure Vessel Sealing System: Revolutionary Hemostasis Product for General Surgery"; Sales/Product Literature 1999.

Sigel et al. "The Mechanism of Blood Vessel Closure by High Frequency Electrocoagulation" Surgery Gynecology & Obstetrics, Oct. 1965 pp. 823-831.

Benaron et al., "Optical Time-Of-Flight and Absorbance Imaging of Biologic Media", Science, American Association for the Advancement of Science, Washington, DC, vol. 259, Mar. 5, 1993, pp. 1463-1466.

(56) References Cited

OTHER PUBLICATIONS

Olsson et al. "Radical Cystectomy in Females" Current Surgical Techniques in Urology, vol. 14, Issue 3, 2001.
"Reducing Needlestick Injuries in the Operating Room"; Sales/Product Literature 2001.
Bergdahl et al. "Studies on Coagulation and the Development of an Automatic Computerized Bipolar Coagulator" J. Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003. (15 pages).
Sengupta et al., "Use of a Computer-Controlled Bipolar Diathermy System in Radical Prostatectomies and Other Open Urological Surgery" ANZ Journal of Surgery (2001) 71.9 pp. 538-540.
Crawford et al. "Use of the LigaSure Vessel Sealing System in Urologic Cancer Surger" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO Worid Congress 2000, Washington, D.C.
U.S. Appl. No. 08/926,869, filed Sep. 10, 1997; inventor: James G. Chandler, Abandoned.
U.S. Appl. No. 09/177,950, filed Oct. 23, 1998; inventor: Randel A. Frazier, abandoned.
U.S. Appl. No. 09/387,883, filed Sep. 1, 1999; inventor: Dale F. Schmaltz, abandoned.
U.S. Appl. No. 09/591,328, filed Jun. 9, 2000; inventor: Thomas P. Ryan, abandoned.
U.S. Appl. No. 12/336,970, filed Dec. 17, 2008; inventor: Paul R. Sremcich, abandoned.
U.S. Appl. No. 14/065,644, filed Oct. 29, 2013; inventor: Reschke, abandoned.
Michael Choti, "Abdominoperineal Resection with the LigaSure Vessel Sealing System and LigaSure Atlas 20 cm Open Instrument"; Innovations That Work, Jun. 2003. (4 pages).
Chung et al., "Clinical Experience of Sutureless Closed Hemorrhoidectomy with LigaSure" Diseases of the Colon & Rectum vol. 46, No. 1 Jan. 2003, pp. 87-92.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte,NC; Date: Aug. 2003. (1 page).
Peterson et al. "Comparison of Healing Process Following Ligation with Sutures and Bipolar Vessel Sealing" Surgical Technology International (2001). (8 pages).
E. David Crawford "Evaluation of a New Vessel Sealing Device in Urologic Cancer Surgery" Sales/Product Literature 2000. (1 page).
Muller et al., "Extended Left Hemicoletomy Using the LigaSure Vessel Sealing System" Innovations That Work, Sep. 1999. (4 pages).
Carus et al., "Initial Experience With The LigaSure Vessel Sealing System in Abdominal Surgery" Innovations That Work, Jun. 2002. (4 pages).
Herman et al., "Laparoscopic Intestinal Resection With the LigaSure Vessel Sealing System: A Case Report"; Innovations That Work, Feb. 2002. (4 pages).
Koyle et al., "Laparoscopic Palomo Varicocele Ligation in Children and Adolescents" Pediatric Endosurgery & Innovative Techniques, vol. 6, No. 1, 2002, pp. 15-19.
LigaSure Vessel Sealing System, the Seal of Confidence in General, Gynecologic, Urologic, and Laparaoscopic Surgery; Sales/Product Literature; Apr. 2002. (8 pages).
Joseph Ortenberg "LigaSure System Used in Laparoscopic 1st and 2nd Stage Orchiopexy" Innovations That Work, Nov. 2002. (4 pages).
Olsson et al. "Radical Cystectomy in Females" Current Surgical Techniques in Urology, vol. 14, Issue 3, 2001. (8 pages).
Levy et al. "Randomized Trial of Suture Versus Electrosurgical Bipolar Vessel Sealing in Vaginal Hysterectomy" Obstetrics & Gynecology, vol. 102, No. 1, Jul. 2003, pp. 147-151.
Michael Choti, "Abdominoperineal Resection with the LigaSure Vessel Sealing System and LigaSure Atlas 20 cm Open Instrument" Innovations That Work, quadrature.Jun. 2003.
Chung et al., "Clinical Experience of Sutureless Closed Hemorrhoidectomy with LigaSure" Diseases of the Colon & Rectum vol. 46, No. Jan. 1, 2003.
Tinkcler L.F., "Combined Diathermy and Suction Forceps", Feb. 6, 1967 (Feb. 6, 1965), British Medical Journal Feb. 6, 1976, vol. 1, nr. 5431 p. 361, ISSN: 0007-1447.
Johnson et al. "Evaluation of the LigaSure Vessel Sealing System in Hemorrhoidectormy" American College of Surgeons (ACS) Clinicla Congress Poster (2000). (1 pages).
Muller et al., "Extended Left Hemicoletomy Using the LigaSure Vessel Sealing System" Innovations That Work,. quadrature.Sep. 1999.
Carus et al., "Initial Experience With the LigaSure Vessel Sealing System in Abdominal Surgery" Innovations That Work,.quadrature. Jun. 2002.
Heniford et al. "Initial Results with an Electrothermal Bipolar Vessel Sealer" Surgical Endoscopy (2000) 15:799-801. (4 pages).
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999, 1 page.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Benaron et al., "Optical Time-Of-Flight and Absorbance Imaging of Biologic Media", Science, American Association for be Advancement of Science, Washington, DC, vol. 259, Mar. 5, 1993, pp. 1463-1466.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
Strasberg et al. "A Phase 1 Study of the LigaSure Vessel Sealing System in Hepatic Surgery" Section of HPB Surger, Washington University School of Medicine, St. Louis MO, Presented at AHPBA, Feb. 2001, 1 page.

(56) References Cited

OTHER PUBLICATIONS

Seyfan et al. "Sutureless Closed Hemorrhoidectomy: A New Technique" Annals of Surgery vol. 234 No. 1, Jul. 2001 pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery"; Grand Rounds in Urology 1999 vol. 1 Issue 4 pp. 10-17.
Craig Johnson. "Use of the LigaSure Vessel Sealing System in Bloodless Hemorrhoidectomy" That Work, Mar. 2000.
Levy et al. "Use of a New Energy-based Vessel Ligation Device During Vaginal Hysterectomy" Int'l Federation of Gynecology and Obstetrics (FIGO) World Congress 1999, 1 page.
Barbara Levy, "Use of a New Vessel Ligation Device During Vaginal Hysterectomy" FIGO 2000, Washington, D.C.. (1 page).
Jarrett et al., "Use of the LigaSure Vessel Sealing System for Peri-Hilar Vessels in Laparoscopic Nephrectomy" Sales/Product Literature 2000, 1 page.
McLellan et al., "Vessel Sealing for Hemostasis During Pelvic Surgery" Int'l Federation of Gynecology and Obstetrics FIGO World Congress 2000, Washington, DC.
McLellan et al. "Vessel Sealing for Hemostasis During Gynecologic Surgery" Sales/Product Literature 1999.
Olsson et al. "Radical Cystectomy in Females" Current Surgical Techniques in Urology, vol. 14, Issue 3; Dated 2001.
"Reducing Needlestick Injuries in the Operating Room" Sales/Product Literature (1 page) Dated: 2001.

\* cited by examiner

SURGICAL INSTRUMENT WITH SENSOR

CROSS REFERENCE TO RELATED APPLICATION

The present application is a continuation of U.S. patent application Ser. No. 16/899,678, filed on Jun. 12, 2020, which is a continuation of U.S. patent application Ser. No. 15/401,227, filed on Jan. 9, 2017, now U.S. Pat. No. 10,695,123, which claims the benefit of and priority to U.S. Provisional Application No. 62/288,962, filed on Jan. 29, 2016. The entire contents of each of which are hereby incorporated herein by reference.

BACKGROUND

1. Technical Field

The present disclosure relates generally to the field of surgical instruments. In particular, the disclosure relates to a surgical instrument including a sensor(s) enabling the determination of the position and/or force associated with components of the surgical instrument.

2. Background of Related Art

Surgical instruments such as electrosurgical forceps are commonly used in open and endoscopic surgical procedures to treat tissue, e.g., coagulate, cauterize, and/or seal tissue. Electrosurgical forceps typically include a pair of jaw members that can be manipulated to grasp targeted tissue. More specifically, the jaw members may be approximated to apply a mechanical clamping force to the tissue, and are associated with at least one electrode to permit the delivery of electrosurgical energy to the tissue.

The combination of mechanical clamping force and electrosurgical energy has been demonstrated to facilitate treating tissue and, specifically, sealing tissue. With respect to mechanical clamping pressure for tissue sealing, for example, it has been found that pressures within the range of about 3 kg/cm$^2$ to about 16 kg/cm$^2$ help ensure formation of effective and consistent tissue seals. Other pressures within or outside this range may be utilized for treating tissue in a different manner and/or for other purposes.

SUMMARY

As used herein, the term "distal" refers to the portion of the instrument or component thereof that is being described that is further from a user, while the term "proximal" refers to the portion of the instrument or component thereof that is being described that is closer to a user. Further, to the extent consistent, any of the aspects described herein may be used in conjunction with any of the other aspects described herein.

Provided in accordance with aspects of the present disclosure is a surgical instrument including a housing, an elongated shaft extending distally from the housing, an end effector disposed at a distal end of the elongated shaft, an actuator operably coupled to the housing, an actuation assembly extending through the housing and the elongated shaft, and a sensor module. The actuation assembly includes a spring, a distal end operably coupled to the end effector or a component associated therewith, and a proximal end operably coupled to the actuator such that actuation of the actuator manipulates the end effector or deploys the component relative thereto. The sensor module is disposed within the housing and configured to sense a property of the spring indicative of an amount the spring has been compressed. The sensor module is further configured, based upon the sensed property, to determine a condition of the end effector or a relative position of the component.

In an aspect of the present disclosure, the end effector includes first and second jaw members movable between an open position and a closed position for grasping tissue therebetween. In such aspects, the condition the sensor module is configured to determine is a clamping pressure applied to tissue grasped between the first and second jaw members.

In another aspect of the present disclosure, the actuation assembly includes a jaw drive rod extending through the housing and the elongated shaft. The jaw drive rod is operably coupled to the first and second jaw members at a distal end of the jaw drive rod. The actuator is operably coupled to a proximal end of the jaw drive rod via a force regulation mechanism including the spring.

In yet another aspect of the present disclosure, the first and second jaw members are configured to supply electrosurgical energy to tissue grasped therebetween to treat tissue.

In still another aspect of the present disclosure, the deployable component includes a knife blade deployable relative to the end effector from a retracted to an extended position. In such aspects, the condition the sensor module is configured to determine is an extent to which the knife blade has been deployed relative to the end effector.

In still yet another aspect of the present disclosure, the actuation assembly includes a link, a carriage, and the spring. The link is operably coupled to the actuator and the carriage is operably coupled between the link and the knife blade such that actuation of the trigger deploys the knife blade from the retracted position to the extended position against a bias of the spring.

In another aspect of the present disclosure, the sensor module includes one or more spring sensors and a processor. The spring sensor(s) is configured to sense the property of the spring indicative of the amount the spring has been compressed and relay the sensed property to the processor to determine the condition of the end effector or the relative position of the component based upon the sensed property. In such aspects, the spring sensor(s) may be configured to sense a change in inductance of the spring indicative of the amount the spring has been compressed. Alternatively, the spring sensor(s) may be configured to sense a spacing between rungs of the spring indicative of the amount the spring has been compressed.

In still another aspect of the present disclosure, the sensor module further includes a storage device configured to store data representing a relationship between the property of the spring indicative of the amount the spring has been compressed and the condition of the end effector or the relative position of the component. The processor, in such aspects, is configured to access the data to determine the condition of the end effector or the relative position of the component based upon the sensed property. The data may be stored in the storage device as a look-up table.

In yet another aspect of the present disclosure, the sensor module includes an output device configured to output an indicator based upon the condition of the end effector or the relative position of the component determined by the processor. The indicator may include includes an audible output, a visual output, and/or a tactile output.

Another surgical instrument provided in accordance with aspects of the present disclosure includes a movable handle movable from an initial position to a compressed position, an end effector remote from the movable handle and movable from an open configuration to a closed configuration for grasping tissue, an actuation assembly including a distal end operably coupled to the end effector and a proximal end, a force regulating mechanism including a spring and operably coupling the movable handle with the proximal end of the actuation assembly such that movement of the movable handle from the initial position to the compressed position moves the end effector from the open configuration to the closed configuration, and a sensor module. The force regulating mechanism is configured to regulate a clamping pressure applied to tissue grasped by the end effector. The sensor module is configured to sense a property of the spring of the force regulating mechanism indicative of an amount the spring has been compressed and, based upon the sensed property, determine the clamping pressure applied to tissue.

In an aspect of the present disclosure, the sensor module includes one or more spring sensors and a processor. The spring sensor(s) is configured to sense the property of the spring indicative of the amount the spring has been compressed and relay the sensed property to the processor to determine the clamping pressure applied to tissue based upon the sensed property.

In another aspect of the present disclosure, the spring sensor(s) is configured to sense a change in inductance of the spring indicative of the amount the spring has been compressed. Alternatively, the spring sensor(s) may be configured to sense a spacing between rungs of the spring indicative of the amount the spring has been compressed.

In yet another aspect of the present disclosure, the sensor module further includes a storage device configured to store data representing a relationship between the property of the spring indicative of the amount the spring has been compressed and the clamping pressure applied to tissue. The processor is configured to access this data to determine the clamping pressure applied to tissue based upon the sensed property. The data may be stored in the storage device as a look-up table.

In still another aspect of the present disclosure, the sensor module includes an output device configured to output an indicator based upon the clamping pressure applied to tissue determined by the processor.

BRIEF DESCRIPTION OF THE DRAWINGS

Various aspects and features of the present disclosure are described herein with reference to the drawings, wherein like reference numerals identify similar or identical components, and wherein.

DETAILED DESCRIPTION

Figure 1:
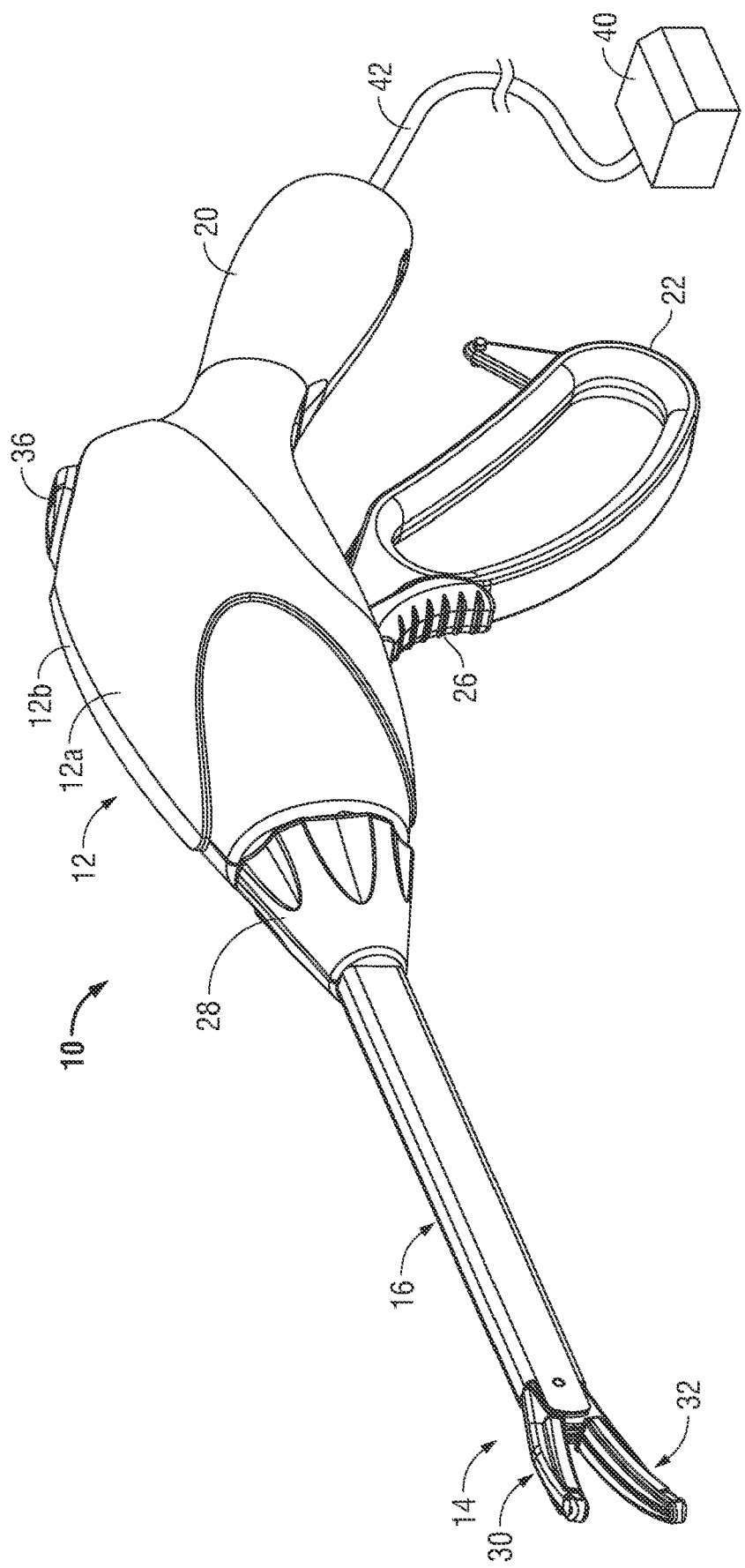
FIG. 1 is a perspective view of a surgical instrument configured for use in accordance with the present disclosure.

Turning to FIG. 1, a surgical instrument 10 configured for use in accordance with the present disclosure is shown generally including a housing 12 that supports various actuators, e.g., a movable handle 22, a trigger 26, a rotation knob 28, and a switch 36, for remotely controlling an end effector assembly 14 through an elongated shaft 16. Although illustrated and described herein as an electrosurgical forceps configured for use in laparoscopic or endoscopic surgical procedures, the aspects and features of the present disclosure are equally applicable for use with other surgical instruments configured for use in traditional open surgical procedures and/or laparoscopic or endoscopic surgical procedures. For the purposes herein, instrument 10 is generally described.

Housing 12 of instrument 10 is constructed of a first housing half 12a and a second housing half 12b. Housing halves 12a, 12b may be constructed of sturdy plastic, or other suitable material, and may be joined to one another by adhesives, ultrasonic welding, or other suitable assembly process. Housing 12 supports a stationary handle 20, a movable handle 22, a trigger 26, and a rotation knob 28. Movable handle 22, as detailed below, is operable to move jaw members 30, 32 of end effector assembly 14 between an open configuration (FIG. 2A), wherein jaw members 30, 32 are disposed in spaced relation relative to one another, and a closed configuration (FIG. 2B), wherein jaw members 30, 32 are approximated relative to one another. More specifically, compression of movable handle 22 towards stationary handle 20 serves to move end effector assembly 14 to the closed configuration and return of movable handle 22 away from stationary handle 20 serves to move end effector assembly 14 back to the open configuration. Trigger 26, as also detailed below, is operable to extend and retract a knife blade 56 (see FIG. 2A) between jaw members 30, 32 when the end effector assembly 14 is in the closed configuration. Rotation knob 28 serves to rotate elongated shaft 16 and end effector assembly 14 relative to housing 12.

To electrically control end effector assembly 14, housing 12 supports a switch 36 thereon, which is operable to initiate and terminate the delivery of electrosurgical energy to end effector assembly 14. Switch 36 is in electrical communication with a source of electrosurgical energy such as electrosurgical generator 40. A cable 42 extends between housing 12 and generator 40 and may include a connector (not shown) thereon such that instrument 10 may be selectively electrically coupled and decoupled from generator 40. In other embodiments, instrument 10 may be configured as a battery-powered instrument wherein generator 40 is mounted on or within instrument 10.

Figure 2A:
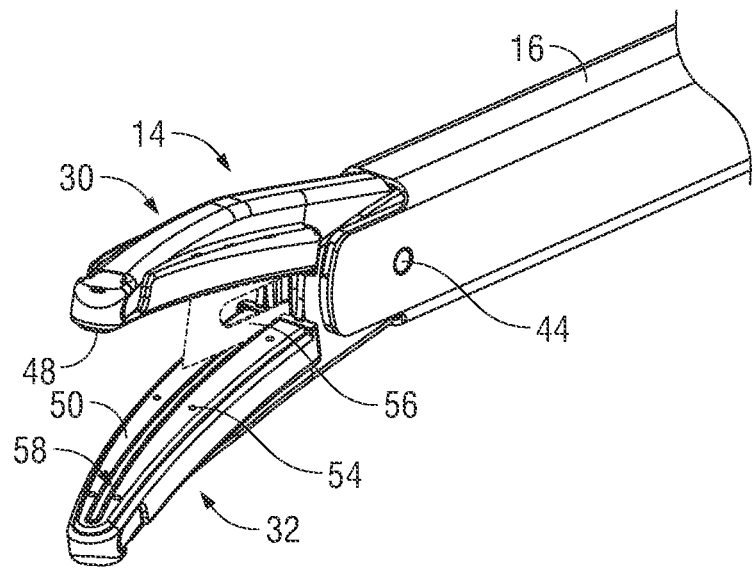
FIG. 2A is an enlarged perspective view of an end effector assembly of the surgical instrument of FIG. 1, wherein jaw members thereof are disposed in an open configuration.
Figure 2B:
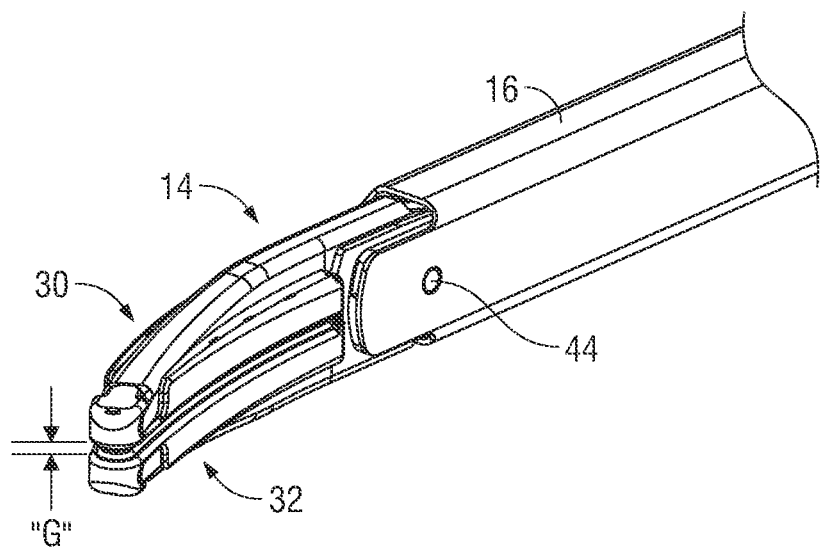
FIG. 2B is an enlarged perspective view of the end effector assembly of the surgical instrument of FIG. 1, wherein the jaw members thereof are disposed in a closed configuration.

Referring to FIGS. 2A and 2B, end effector assembly 14 includes first and second jaw members 30, 32 mechanically coupled to the distal end of elongated shaft 16 about a pivot pin 44. Jaw members 30, 32 are electrically coupled to cable 42 and, thus, generator 40 (FIG. 1) via wires (not shown) extending through elongated shaft 16. Electrically-conductive plates 48, 50 of jaw members 30, 32, respectively are electrically coupled to opposite terminals, e.g., positive (+) and negative (−) terminals, associated with generator 40. Thus, bipolar energy may be conducted through tissue grasped between plates 48, 50 of jaw members 30, 32, respectively, to treat tissue. Alternatively, end effector assembly 14 may be configured for delivering monopolar energy to the tissue for use in connection with a return pad (not shown) remotely positioned on the patient. Other forms of energy, e.g., ultrasonic, microwave, thermal, light, etc. may additionally or alternatively be used to facilitate tissue treatment.

As noted above, jaw members 30, 32 are pivoted about pivot pin 44 and relative to elongated shaft 16 between the open configuration (FIG. 2A) and the closed configuration (FIG. 2B). In the closed configuration of end effector assembly 14 (FIG. 2B), electrically-conductive plates 48, 50 of jaw members 30, 32 provide a clamping pressure to the tissue grasped therebetween. Also, in the closed configuration, a minimum gap distance "G" may be maintained between electrically-conductive plates 48, 50 by one or more stop members 54 disposed on either or both electrically-conductive plates 48, 50.

Figure 3A:
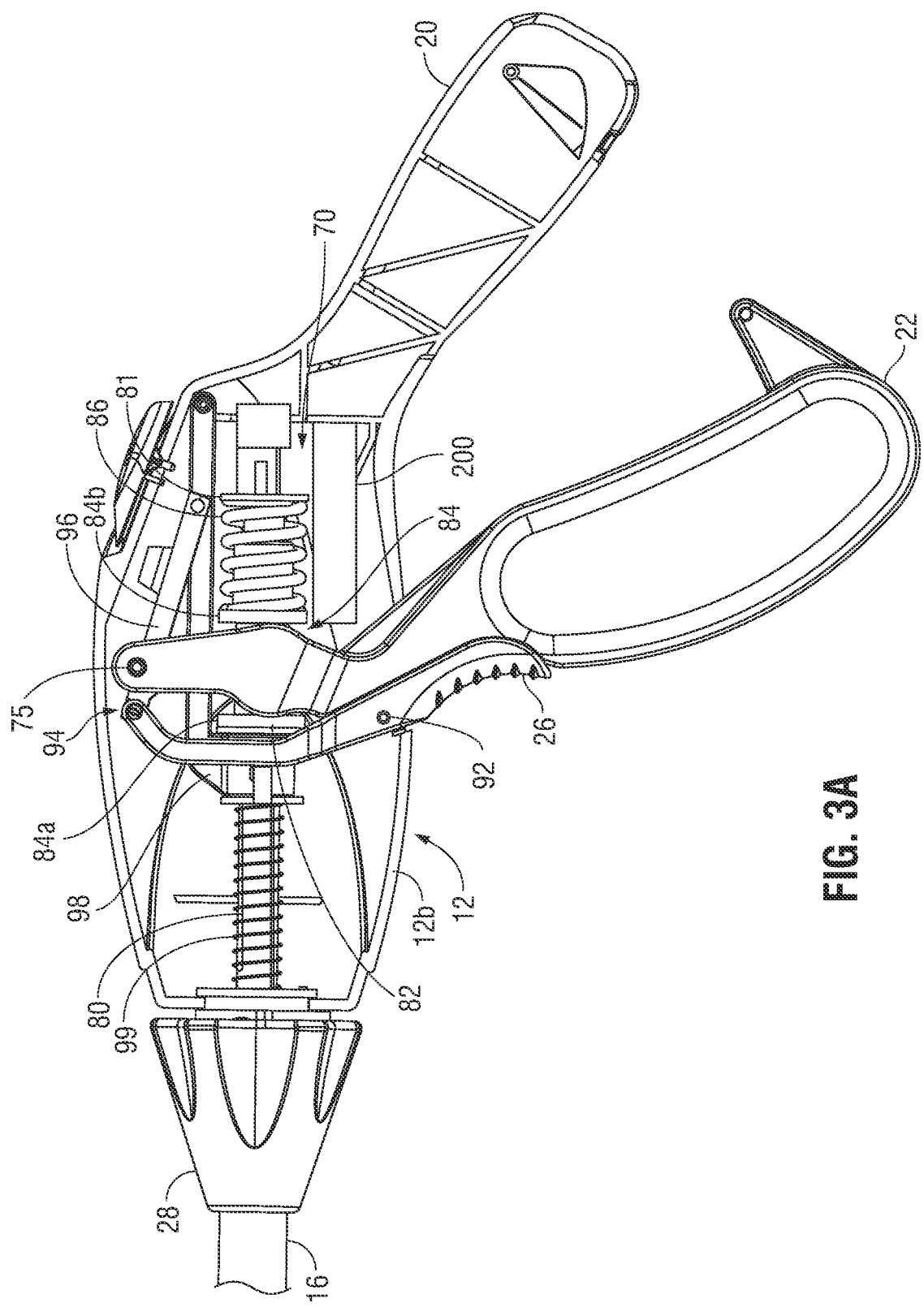
FIG. 3A is a side view of a proximal portion of the surgical instrument of FIG. 1 with a portion of a housing removed to illustrate the internal components thereof, wherein a movable handle is disposed in an initial position corresponding to the open configuration of the jaw members.
Figure 3B:
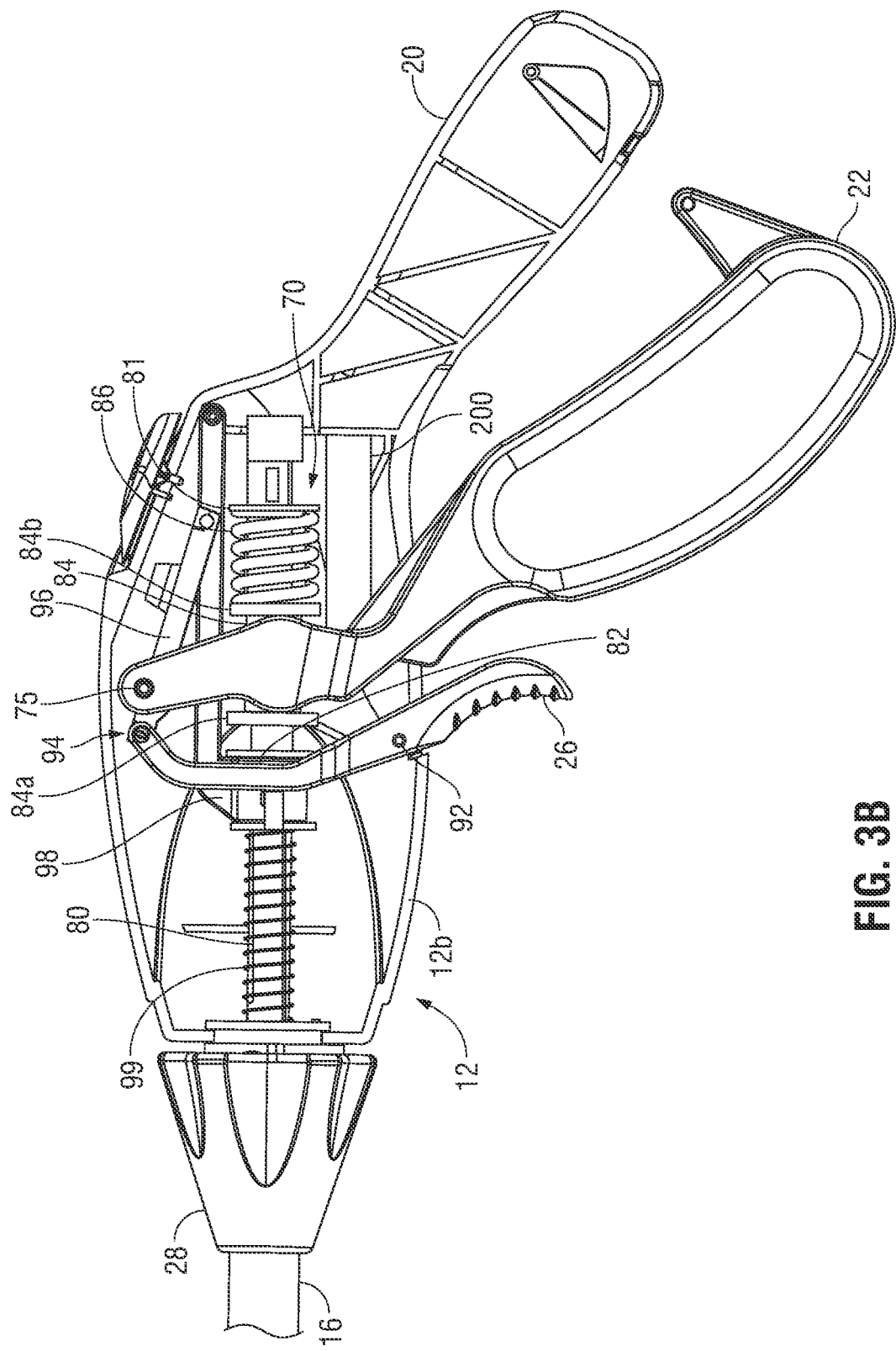
FIG. 3B is a side view of the proximal portion of the surgical instrument of FIG. 1 with a portion of the housing removed to illustrate the internal components thereof, wherein the movable handle is disposed in an intermediate position corresponding to a partially-closed configuration of the jaw members.
Figure 3C:
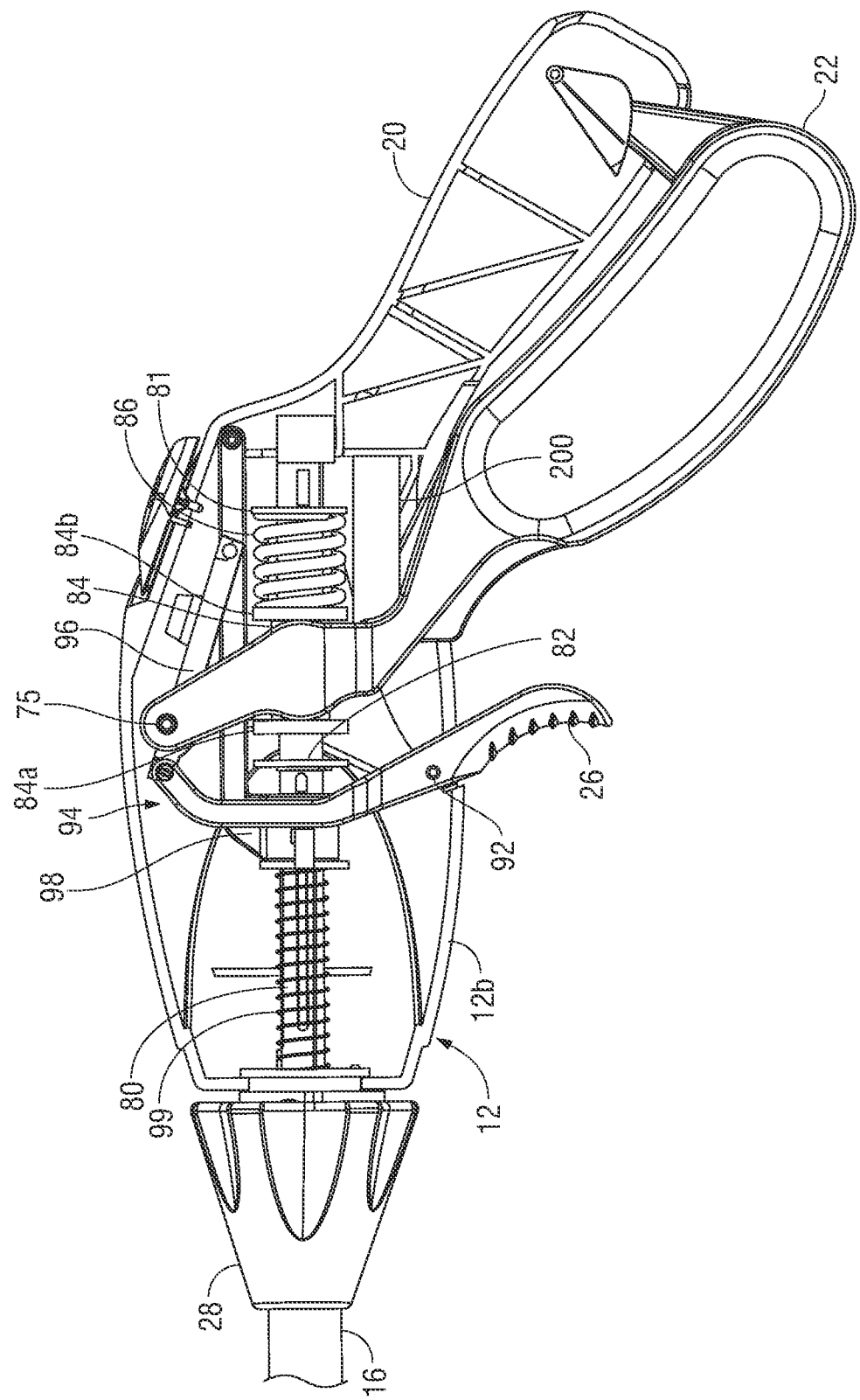
FIG. 3C is a side view of the proximal portion of the surgical instrument of FIG. 1 with a portion of the housing removed to illustrate the internal components thereof, wherein the movable handle is disposed in a compressed position corresponding to the closed configuration of the jaw members.

Referring to FIGS. 3A-3C, in conjunction with FIGS. 2A and 2B, a drive assembly 70 operably couples movable handle 22 with end effector assembly 14 such that, as noted above, movable handle 22 is operable to move jaw members 30, 32 of end effector assembly 14 between the open configuration (FIG. 2A) and the closed configuration (FIG. 2B). Drive assembly 70 includes a jaw drive rod 80 slidably disposed within elongated shaft 16. The distal end of jaw drive rod 80 is operably coupled to jaw members 30, 32, e.g., via a pin (not shown) associated with jaw drive rod 80 and extending through oppositely-angled slots (not shown) defined within proximal flanges (not shown) of jaw members 30, 32, such that proximal sliding of jaw drive rod 80 through elongated shaft 16 moves end effector assembly 14 from the open configuration to the closed configuration. However, the opposite configuration is also contemplated, as are other mechanisms for operably coupling jaw drive rod 80 with jaw members 30, 32.

The proximal end of jaw drive rod 80 extends into housing 12. Drive assembly 70 further includes a proximal stop ring 81 fixedly engaged about jaw drive rod 80 within housing 12, a distal stop ring 82 fixedly engaged about jaw drive rod 80 within housing 12, and a mandrel 84 slidably disposed about jaw drive rod 80 within housing 12 and positioned between proximal and distal stop rings 81, 82, respectively. A spring 86 of drive assembly 70 is disposed about jaw drive rod 80 and positioned between proximal stop ring 81 and mandrel 84. Spring 86 biases mandrel 84 distally along jaw drive rod 80 into contact with distal stop ring 82, which inhibits further distal sliding of mandrel 84 about jaw drive rod 80.

Movable handle 22 is pivotably coupled within housing 12 via a pivot pin 75 and is operably coupled to jaw drive rod 80 by way of mandrel 84 such that movable handle 22 may be manipulated to impart longitudinal motion to jaw drive rod 80. As noted above, longitudinal movement of jaw drive rod 80, in turn, moves end effector assembly 14 between the open and closed configurations (FIGS. 2A and 2B, respectively). More specifically, a portion of movable handle 22 is operably retained between distal and proximal rims 84a, 84b, respectively, of mandrel 84 such that pivoting of movable handle 22 towards stationary handle 20 urges mandrel 84 proximally through housing 12 and elongated shaft 16 and such that pivoting of movable handle 22 away from stationary handle 20 urges mandrel 84 distally through housing 12. Distal longitudinal motion of mandrel 84, in response to pivoting of movable handle 22 away from stationary handle 20, is transmitted directly into distal translation of jaw drive rod 80 through housing 12 and elongated shaft 16 due to the abutment mandrel 84 with distal stop ring 82. As noted above, such movement of jaw drive rod 80 results in the return of jaw members 30, 32 towards the open condition (FIG. 2A).

Proximal longitudinal motion of mandrel 84, in response to pivoting of movable handle 22 towards stationary handle 20, initially effects a corresponding proximal motion of jaw drive rod 80 through housing 12 and elongated shaft 16 to thereby move jaw members 30, 32 towards the closed condition (FIG. 2B). During this initial movement, jaw members 30, 32 meet minimal resistance as they move towards the closed condition (FIG. 2B) and, thus, spring 86 remains in its initial condition, e.g., an initial pre-compressed condition or, in some embodiments, an un-compressed condition. However, once jaw members 30, 32 are closed about tissue, where mechanical stops (not explicitly shown) associated with end effector assembly 14 or the distal end of jaw drive rod 80 have been reached, and/or where jaw members 30, 32 otherwise meet sufficient resistance, further pivoting of movable handle 22 towards stationary handle 20 translates mandrel 84 proximally through housing 12 relative to jaw drive rod 80, rather than moving jaw drive rod 80 in conjunction therewith. In order to permit this relative sliding between mandrel 84 and jaw drive rod 80, spring 86 is compressed. The compression of spring 86 serves as a force-regulator to ensure than an appropriate clamping pressure is applied to tissue grasped between plates 48, 50 of jaw members 30, 32. For tissue sealing, for example, this pressure may be within the range of about 3 kg/cm$^2$ to about 16 kg/cm$^2$; however, other suitable pressures may also be provided.

As noted above, the compression of spring 86 enables regulation of the clamping pressure applied to tissue grasped between plates 48, 50 of jaw members 30, 32. In fact, the amount spring 86 is compressed is indicative of the clamping pressure applied to tissue. Accordingly, as detailed below, a sensor module 200 is incorporated into instrument 10 to determine the amount of compression of spring 86 and, based upon that information, determine the clamping pressure applied to tissue.

Figure 4:
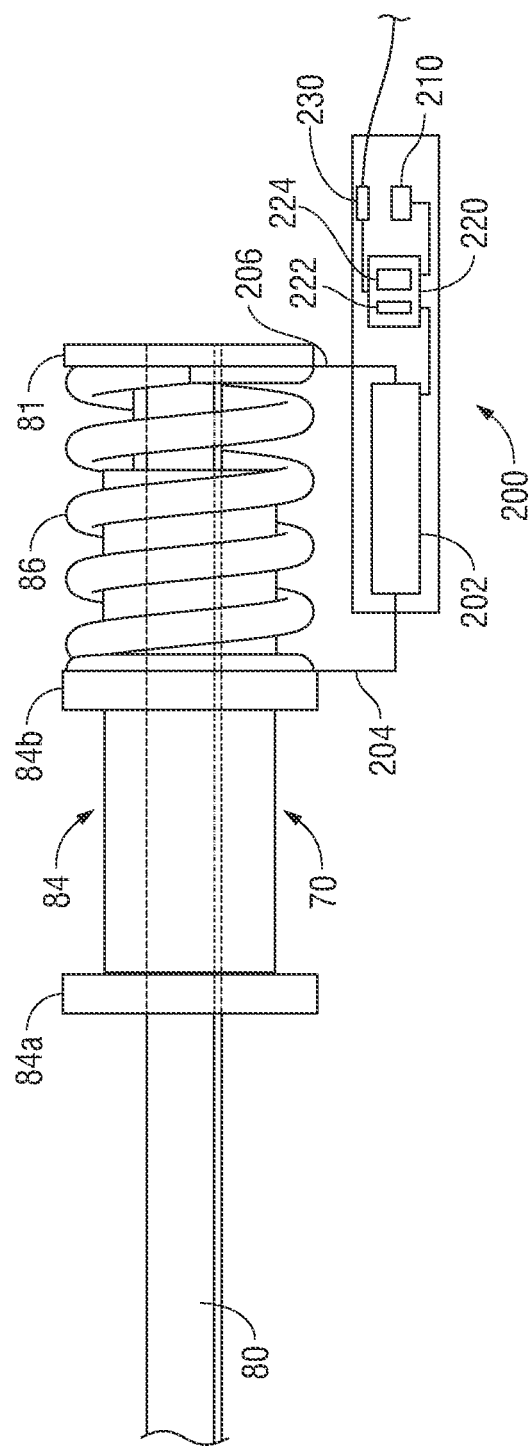
FIG. 4 is a partial, side view of the proximal portion of a jaw actuation mechanism of the surgical instrument of FIG. 1, illustrating a spring sensor provided in accordance with the present disclosure shown operably coupled with the jaw actuation mechanism.

Referring to FIG. 4, sensor module 200 is mounted within housing 12 (FIGS. 3A-3C) adjacent spring 86 and generally includes a spring sensor 202, a storage device 210, a CPU 220 including a memory 222 and a processor 224, and an output device 230. Spring sensor 202 is electrically coupled to a first end of spring 86 via lead wire 204 and to a second end of spring 86 via lead wire 206 and includes internal components (not explicitly shown) configured to measure a change in inductance of spring 86. Since the inductance of a spring changes as the spring is compressed, measuring the change in inductance of spring 86 can be used to determine the extent to which spring 86 has been compressed. Sensors suitable for this purpose include those detailed in Intl. Appln. Pub. No. WO 2008/090338, filed on Jan. 23, 2008, the entire contents of which are hereby incorporated herein by reference. The change in inductance sensed by spring sensor 202 is relayed to CPU 220.

The relationship between the change in inductance of spring 86 and the amount of compression of spring 86 can be determined empirically and/or experimentally. Likewise, the relationship between the amount of compression of spring 86 and the clamping pressure applied to tissue can be determined, empirically and/or experimentally. Putting this data together, the relationship between the change in inductance of spring 86 and the clamping pressure applied to tissue can be determined. Alternatively, the relationship between the change in inductance of spring 86 and the clamping pressure applied to tissue can be determined, empirically and/or experimentally, without the intermediate step of determining the relationships of these metrics with the compression of spring 86. In either instance, such relationship data can be stored, for example, as a look-up table in storage device 210 of sensor module 200.

Storage device 210 of sensor module 200 may include any suitable component(s) operable for storing information, e.g., the look-up table including information indicating the relationship between the change in inductance of spring 86, the amount of compression of spring 86, and/or the resultant clamping pressure applied to tissue, such as, for example, a magnetic disk, flash memory, optical disk, or other suitable data storage device.

CPU 220 of sensor module 220 is configured to receive the change in inductance sensed by spring sensor 202. Memory 222 of CPU 220 may include any computer memory, e.g., RAM or ROM, mass storage media, removable storage media, combinations thereof, or any other suitable computer-readable storage medium, storing instructions for causing processor 224 to execute particular functions, e.g., to access the look-up table stored in storage device 210 of sensor module 200 and determine the clamping pressure corresponding to the change in inductance sensed by spring sensor 202 (directly or by way of the amount of compression of spring 86). Processor 224 may further be configured to determine whether the corresponding clamping pressure is within an appropriate clamping pressure range. The appropriate clamping pressure range may also be stored in storage device 210 and accessible by processor 224 for comparison with the determined clamping pressure.

In embodiments where processor 224 determines whether the determined clamping pressure is within the appropriate clamping pressure range, processor 224 may further be configured to direct output device 230 to provide a notification indicating whether the determined clamping pressure is or is not within the appropriate clamping pressure range. For example, output device 230 may emit an audible tone, activate a visual indicator, provide a tactile response, etc. when the determined clamping pressure is within the appropriate clamping pressure range. Once alerted to the fact that an appropriate clamping pressure has been applied, the surgeon can confidently initiate the supply of electrosurgical energy to end effector assembly 14 (FIGS. 2A and 2B) to treat the grasped tissue. Output device 230 may, alternatively or additionally, be configured to communicate with generator 40 (FIG. 1) such that the supply of electrosurgical energy may automatically be initiated upon reaching a suitable clamping pressure and/or such that an appropriate energy-delivery algorithm is utilized based upon the clamping pressure or clamping pressure range determined. In embodiments where processor 224 does not determine whether the clamping pressure is within the appropriate clamping pressure range, processor 224 may be configured to direct output device 230 to provide a notification indicating the particular clamping pressure that has been determined. Output 230, in such instances, for example, may transmit suitable information to generator 40 (FIG. 1) to enable display of the clamping pressure on the display screen of generator 40 (FIG. 1) or to inhibit the supply of electrosurgical energy until an appropriate clamping pressure is applied or until an override is input to generator 40 (FIG. 1).

As detailed above, sensor module 200 enables a surgeon to be readily apprised of the clamping pressure applied to tissue and/or whether the clamping pressure is within an appropriate clamping pressure range. By providing a sensor module 200 capable of determining the clamping pressure applied to tissue based upon a condition of spring 86, which is disposed in housing 12 and remote from end effector assembly 14, the need for providing such sensors in or around end effector assembly 14, wherein spatial, temperature, environmental, and other considerations result in design challenges and increased manufacturing costs, is obviated.

As an alternative to spring sensor 202 measuring a change in inductance to determine the condition of spring 86, spring sensor 202 may be configured as a hall-effect sensor configured to determine the condition of spring 86 and, based thereon, determine the clamping pressure applied to tissue, similarly as detailed above.

Further, in addition to sensor module 200 determining the clamping pressure applied to tissue, sensor module 200 and/or additional sensors (not explicitly shown) may be utilized, in conjunction with the determined clamping pressure applied, to provide additional information to generator 40 (FIG. 1) for determining an appropriate energy-delivery algorithm to be utilized. For example, the thickness of grasped tissue may be determined by sensor module 200 (or other suitable sensor) and the impedance of grasped tissue may be determined by impedance sensors (not shown) within generator 40. With clamping pressure, tissue thickness, and tissue impedance measurements, a look-up table or other suitable component(s) of storage device 210 and/or generator 40 (FIG. 1), for storing empirical and/experimental data of such measurements, may be consulted to determine the appropriate energy-delivery algorithm to be utilized based upon these three measurements. Notably, sensor module 200 and/or the additional sensors (not explicitly shown) need not cease operation once the supply of electrosurgical energy has been initiated. More specifically, since tissue properties change during the application of electrosurgical energy thereto, feedback, as determined by a change in clamping pressure detected by sensor module 200, a change in tissue thickness detected by sensor module 200 or other suitable sensor (not shown), and/or a change in tissue impedance, may be utilized to ensure that an appropriate energy-deliver algorithm is utilized throughout the entire tissue-treatment process.

Figure 5:
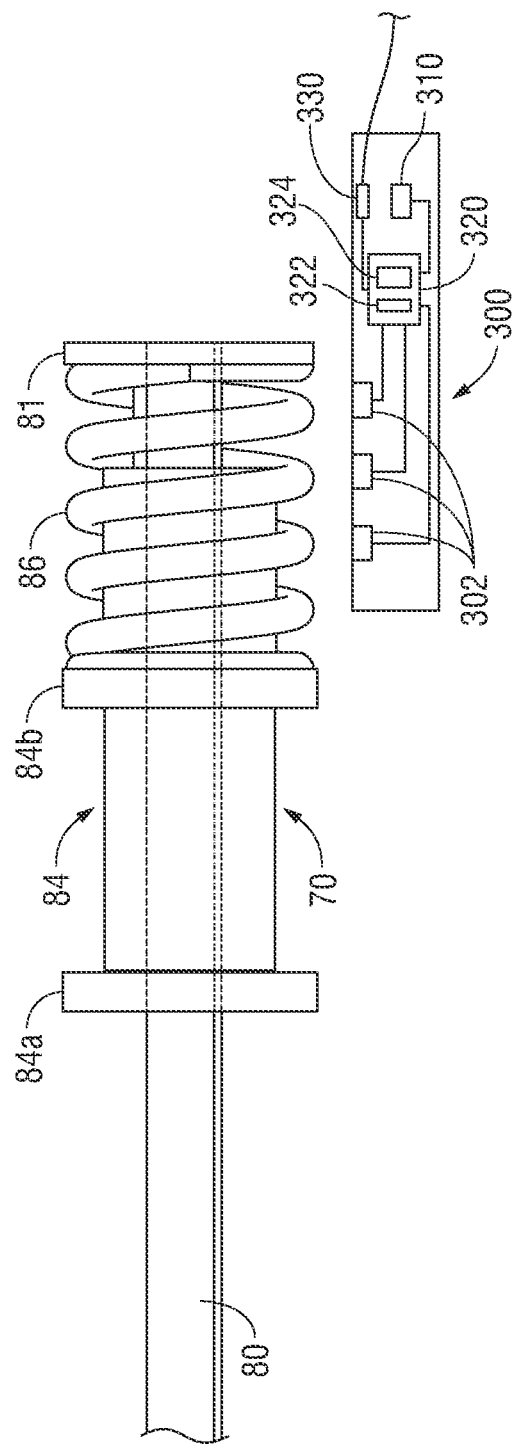
FIG. 5 is a partial, side view of the proximal portion of the jaw actuation mechanism of the surgical instrument of FIG. 1, illustrating another spring sensor provided in accordance with the present disclosure shown operably coupled with the jaw actuation mechanism.

Turning to FIG. 5, another embodiment of a sensor module 300 provided in accordance with the present disclosure is shown configured for use with spring 86 for determining the compression thereof and, based upon such a determination, the clamping pressure applied to tissue. Sensor module 300 is similar to sensor module 200 (FIG. 4) in that it includes a storage device 310, a CPU 320 including a memory 322, a processor 224, and an output device 330. These common components are similar to those of sensor module 200 (FIG. 4) and, thus, will not be detailed again to avoid unnecessary repetition. Rather, only differences between sensor module 300 and sensor module 200 (FIG. 4) will be detailed below.

Sensor module 300 differs from sensor module 200 (FIG. 4) in that, rather than sensing the change in inductance of spring 86, sensor module 300 includes one or more optical sensors 302, e.g., one or more optical encoder sensors, configured to sense a spacing between the rungs of spring 86. The one or more optical sensors 302 may be configured to sense the spacing between any or all pairs of adjacent rungs of spring 86 and determine an average spacing therebetween. Similarly as with inductance, the average spacing between the rungs of spring 86 can be correlated to an amount of compression of spring 86. As noted above, the amount of compression of spring 86, in turn, can be utilized to determine the clamping pressure applied to tissue based on data obtained empirically or via experimentation. Sensor module 300 may otherwise be used similarly as detailed above with respect to sensor module 200 (FIG. 4).

With additional reference to FIGS. 3A-3C, sensor module 300 (and/or sensor module 200 (FIG. 4)) may further be configured such that one or more of sensors 302 is capable of sensing the position of movable handle 22. This may be accomplished by sensing the position of jaw drive rod 80 or a component fixed thereto, e.g., proximal stop ring 81. The position of movable handle 22 may be communicated to generator 40 (FIG. 1) such that the supply of electrosurgical energy from generator 40 (FIG. 1) may be initiated in accordance with the position of movable handle 22, e.g., when movable handle 22 is sufficiently compressed relative to fixed handle 20. Additionally or alternatively, the position of movable handle 22 may be utilized, in connection with the determined clamping pressure and/or other measurements, to further refine the energy-delivery algorithm used, e.g., based upon whether a slow-jaw-closure technique is being utilized during tissue treatment.

Referring to FIGS. 3A-3C, trigger 26 may be manipulated to impart longitudinal motion to knife blade 56 to advance knife blade 56 through knife channel(s) 58 defined within one or both of the jaw members 30, 32 (see FIG. 2A). Trigger 26 is pivotally supported in housing 12 via a pivot pin 92 and is operably coupled to knife blade 56 (FIG. 2A) by a connection mechanism 94. Connection mechanism 94 includes a link 96 and a carriage 98 having the proximal end of knife blade 56 (FIG. 2A) engaged therein. A spring 99 is disposed between the distal end of housing 12 and carriage 98 so as to bias carriage 98 proximally, thereby biasing knife blade 56 towards a retracted position, wherein knife blade 56 is positioned proximally of jaw members 30, 32 (see FIG. 2A), and trigger 26 proximally towards an un-actuated position. Upon actuation of trigger 26, e.g., upon pivoting of trigger 26 towards movable handle 22, linkage 96 is pulled distally to thereby urge carriage 98 distally through housing 12. Distal urging of carriage 98, in turn, compresses spring 99 and advances knife blade 56 distally between jaw members 30, 32 (see FIG. 2A) to cut tissue grasped therebetween.

With respect to deployment of knife blade 56 via actuation of trigger 26, due to the above-detailed configuration, the amount of compression of spring 99 is related to the extent to which knife blade 56 has been deployed. Accordingly, as with sensor modules 200, 300 and spring 86 (FIGS. 4 and 5), a sensor module similar to sensor modules 200, 300 (FIGS. 4 and 5) may be utilized in connection with spring 99 to indicate to a surgeon the extent to which knife blade 56 has been deployed. In fact, sensor modules similar to sensor modules 200, 300 (FIGS. 4 and 5) may be provided in accordance with the present disclosure for use with a suitable spring of a surgical instrument to indicate the position and/or force associated with an end effector assembly and/or deployable component of the surgical instrument.

The above-detailed aspects and features of the present disclosure may be configured to work with robotic surgical systems and what is commonly referred to as "Telesurgery." Such systems employ various robotic elements to assist the surgeon and allow remote operation (or partial remote operation) of surgical instrumentation. Various robotic arms, gears, cams, pulleys, electric and mechanical motors, etc. may be employed for this purpose and may be designed with a robotic surgical system to assist the surgeon during the course of an operation or treatment. Such robotic systems may include remotely steerable systems, automatically flexible surgical systems, remotely flexible surgical systems, remotely articulating surgical systems, wireless surgical systems, modular or selectively configurable remotely operated surgical systems, etc.

The robotic surgical systems may be employed with one or more consoles that are next to the operating theater or located in a remote location. In this instance, one team of surgeons or nurses may prep the patient for surgery and configure the robotic surgical system with one or more of the instruments disclosed herein while another surgeon (or group of surgeons) remotely control the instruments via the robotic surgical system. As can be appreciated, a highly skilled surgeon may perform multiple operations in multiple locations without leaving his/her remote console which can be both economically advantageous and a benefit to the patient or a series of patients.

The robotic arms of the surgical system are typically coupled to a pair of master handles by a controller. The handles can be moved by the surgeon to produce a corresponding movement of the working ends of any type of surgical instrument (e.g., end effectors, graspers, knifes, scissors, etc.) which may complement the use of one or more of the embodiments described herein. The movement of the master handles may be scaled so that the working ends have a corresponding movement that is different, smaller or larger, than the movement performed by the operating hands of the surgeon. The scale factor or gearing ratio may be adjustable so that the operator can control the resolution of the working ends of the surgical instrument(s).

The master handles may include various sensors to provide feedback to the surgeon relating to various tissue parameters or conditions, e.g., tissue resistance due to manipulation, cutting or otherwise treating, pressure by the instrument onto the tissue, tissue temperature, tissue impedance, etc. As can be appreciated, such sensors provide the surgeon with enhanced tactile feedback simulating actual operating conditions. The master handles may also include a variety of different actuators for delicate tissue manipulation or treatment further enhancing the surgeon's ability to mimic actual operating conditions.

Figure 6:
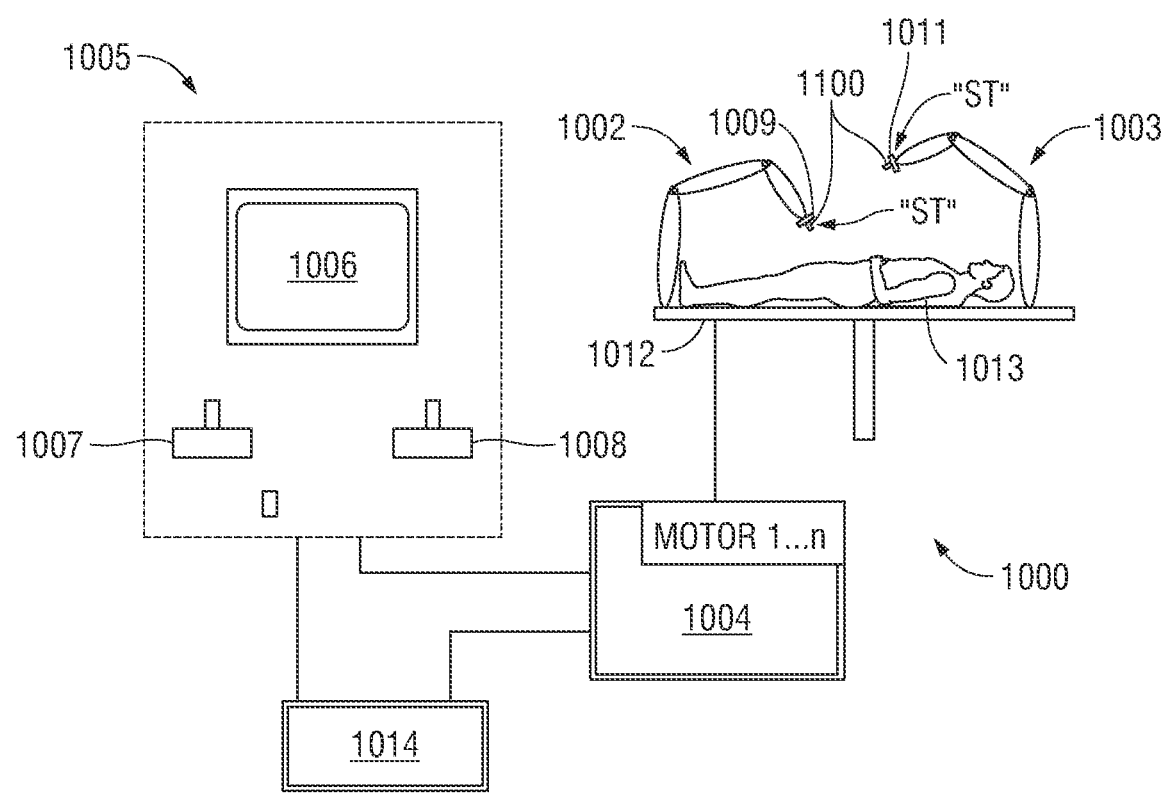
FIG. 6 is a schematic illustration of a robotic surgical system configured for use in conjunction with aspects and features of the present disclosure.

Turning to FIG. 6, a medical work station is shown generally as work station 1000 and generally may include a plurality of robot arms 1002, 1003; a control device 1004; and an operating console 1005 coupled with control device 1004. Operating console 1005 may include a display device 1006, which may be set up in particular to display threedimensional images; and manual input devices 1007, 1008, by means of which a surgeon may be able to telemanipulate robot arms 1002, 1003 in a first operating mode.

Each of the robot arms 1002, 1003 may include a plurality of members, which are connected through joints, and an attaching device 1009, 1011, to which may be attached, for example, a surgical tool "ST" supporting an end effector 1100, in accordance with any one of several embodiments disclosed herein, as will be described in greater detail below.

Robot arms 1002, 1003 may be driven by electric drives (not shown) that are connected to control device 1004. Control device 1004 (e.g., a computer) may be set up to activate the drives, in particular by means of a computer program, in such a way that robot arms 1002, 1003, their attaching devices 1009, 1011 and thus the surgical tool (including end effector 1100) execute a desired movement according to a movement defined by means of manual input devices 1007, 1008. Control device 1004 may also be set up in such a way that it regulates the movement of robot arms 1002, 1003 and/or of the drives.

Medical work station 1000 may be configured for use on a patient 1013 lying on a patient table 1012 to be treated in a minimally invasive manner by means of end effector 1100. Medical work station 1000 may also include more than two robot arms 1002, 1003, the additional robot arms likewise being connected to control device 1004 and being telemanipulatable by means of operating console 1005. A medical instrument or surgical tool (including an end effector 1100) may also be attached to the additional robot arm. Medical work station 1000 may include a database 1014, in particular coupled to with control device 1004, in which are stored, for example, pre-operative data from patient/living being 1013 and/or anatomical atlases.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as examples of particular embodiments. Those skilled in the art will envision other modifications within the scope and spirit of the claims appended hereto.

Although the foregoing disclosure has been described in some detail by way of illustration and example, for purposes of clarity or understanding, it will be obvious that certain changes and modifications may be practiced within the scope of the appended claims.

What is claimed is:

1. A surgical system, comprising:
   an actuation assembly, including:
      an actuator;
      a drive rod; and
      a force-regulating spring operably coupled between the actuator and the drive rod and configured to regulate a force applied by the drive rod in response to actuation of the actuator;
   a sensor module configured to sense a change in inductance of the force-regulating spring and relay to a processor an amount of the sensed change; and
   an end effector including first and second jaw members movable between an open position and a closed position for grasping tissue therebetween in response to movement of the drive rod,
   wherein the processor associates the amount of sensed change in inductance with a known clamping force being applied on tissue by the first and second jaw members in the closed position.

2. The surgical system according to claim 1, wherein the sensor module further includes a storage device configured to store data representing a relationship between the sensed property and the force applied by the drive rod, the processor configured to access the data to determine the force applied by the drive rod based upon the sensed property, the processor configured to determine if the force applied by the drive rod and resulting clamping force applied by the first and second jaw members to tissue is within an acceptable range stored in the storage device and, if so, alert the surgeon to treat tissue grasped between the jaw members.

3. The surgical system according to claim 2, further comprising an output device configured to output an indicator based upon the determined force applied.

4. The surgical system according to claim 3, wherein the indicator includes at least one of an audible output, a visual output, or a tactile output.

5. A surgical system, comprising:
   a housing;
   a shaft extending distally from the housing;
   an end effector disposed at a distal end portion of the shaft, the end effector including first and second jaw movable between an open position and a closed position for grasping tissue and applying a clamping force to the grasped tissue;
   an actuation assembly, including:
      an actuator coupled to the housing;
      a drive rod coupled to the first and second jaw members such that translation of the drive rod moves the first and second jaw movable between the open position and the closed position to grasp the tissue and apply the clamping force to the grasped tissue; and
      a force-regulating spring disposed within the housing and operably coupled between the actuator and the drive rod, the force-regulating spring configured to regulate the clamping force applied to tissue; and
   a sensor module disposed within the housing and configured to sense a change in inductance of the actuation assembly and relay to a processor an amount of the sensed change,
   wherein the processor associates the amount of sensed change in inductance with a known clamping force being applied on tissue by the first and second jaw members in the closed position.

6. The surgical system according to claim 5, wherein the surgical system is a robotic surgical system including an operating console having one or more input devices which are configured to communicate with the actuation assembly to transition the end effector between the open and closed positions.

7. The surgical system according to claim 6, wherein the operating console communicates with a control device operably connected to a robot arm engaged to the housing, the control device configured to coordinate movement between the one or more input devices, the robot arm, and the end effector.

8. The surgical system according to claim 5, wherein the housing includes a handle and wherein movement of the handle correspondingly biases the drive rod against the force-regulating spring to move the first and second jaw members between the open and closed positions.

9. The surgical system according to claim 5, wherein the sensor module further includes a storage device configured to store data representing a relationship between the sensed property and the force applied to the grasped tissue, the processor configured to access the data to determine the force applied to the grasped tissue based upon the sensed property, the processor configured to access the data to determine the force applied by the drive rod based upon the sensed property, the processor configured to determine if the force applied by the drive rod and resulting clamping force applied by the first and second jaw members to tissue is within an acceptable range stored in the storage device and, if so, alert the surgeon to treat tissue grasped between the jaw members.

10. The surgical system according to claim 1, wherein the surgical system is a robotic surgical system including an operating console having one or more input devices which are configured to communicate with the actuation assembly to transition the end effector between the open and closed positions.

11. The surgical system according to claim 10, wherein the operating console communicates with a control device operably connected to a robot arm engaged to the actuation assembly, the control device configured to coordinate movement between the one or more input devices, the robot arm, and the end effector.

12. The surgical system according to claim 1, wherein the actuator includes a handle and wherein movement of the handle correspondingly biases the drive rod against the force-regulating spring to move the first and second jaw members between the open and closed positions.

13. A surgical system, comprising:
a housing;
a shaft extending distally from the housing;
an end effector disposed at a distal end portion of the shaft, the end effector movable between an open position and a closed position for grasping tissue and applying a force to the grasped tissue;
an actuation assembly, including:
an actuator coupled to the housing;
a drive rod coupled to end effector such that translation of the drive rod transitions the end effector between the open position and the closed position to grasp the tissue and apply the force to the grasped tissue; and
a force-regulating spring disposed within the housing and operably coupled between the actuator and the drive rod, the force-regulating spring positioned about the drive rod, the force-regulating spring configured to regulate the force applied to tissue; and
a sensor module disposed within the housing and configured to sense a property a change in inductance of the actuation assembly to determine the force applied to the grasped tissue based upon the sensed property and relay to a processor an amount of the sensed change,
wherein the processor associates the amount of sensed change in inductance with a known clamping force being applied on tissue by the first and second jaw members in the closed position.

14. The surgical system according to claim 13, wherein the sensor module further includes a storage device configured to store data representing a relationship between the sensed property and the force applied to the grasped tissue, the processor configured to access the data to determine the force applied to the grasped tissue based upon the sensed property, the processor configured to determine if the force applied by the drive rod and resulting clamping force applied by the first and second jaw members to tissue is within an acceptable range stored in the storage device and, if so, alert the surgeon to treat tissue grasped between the jaw members.

15. The surgical system according to claim 13, wherein the surgical system is a robotic surgical system including an operating console having one or more input devices which are configured to communicate with the actuation assembly to transition the end effector between the open and closed positions.

16. The surgical system according to claim 15, wherein the operating console communicates with a control device operably connected to a robot arm engaged to the housing, the control device configured to coordinate movement between the one or more input devices, the robot arm, and the end effector.

17. The surgical system according to claim 13, wherein the housing includes a handle and wherein movement of the handle correspondingly biases the drive rod against the force-regulating spring to move the first and second jaw members between the open and closed positions.

* * * * *